United States Patent [19]

Fung et al.

[11] Patent Number: 4,855,225
[45] Date of Patent: Aug. 8, 1989

[54] METHOD OF DETECTING ELECTROPHORETICALLY SEPARATED OLIGONUCLEOTIDES

[75] Inventors: Steven Fung, Palo Alto; Sam L. Woo, Redwood City, both of Calif.; Richard P. Haugland, Junction City, Oreg.; Steven M. Menchen, Hayward; Charles R. Connell, Redwood City, both of Calif.

[73] Assignee: Applied Biosystems, Inc., Foster City, Calif.

[21] Appl. No.: 827,348

[22] Filed: Feb. 7, 1986

[51] Int. Cl.$^4$ ............... C12Q 1/68; G01N 33/50; C07H 21/00
[52] U.S. Cl. ............... 435/6; 536/26; 536/27; 536/28; 935/88; 935/77
[58] Field of Search ............... 435/6; 536/26-28; 935/77, 88

[56] References Cited

U.S. PATENT DOCUMENTS 4,318,846 3/1982 Khanna et al. ............... 260/112 B
4,415,732 11/1983 Caruthers et al. ............... 536/27
4,458,066 7/1984 Caruthers et al. ............... 536/27

FOREIGN PATENT DOCUMENTS 3501306 7/1985 Fed. Rep. of Germany .
2153356 8/1985 United Kingdom .
2155176 9/1985 United Kingdom .

OTHER PUBLICATIONS

A Stanley Jones, Christopher McGuigan and Richard T. Walker "Synthesis of some Nucleoside Cyclic Phosphoramidates and Related Compounds via Phosphoramidites" J. Chem. Soc. Perkin Trans. I 1985 pp. 199-202.
"Andre Chollet and Eric H. Kawashima Biotin-labeled Synthetic Oligo-Deoxyribonucleotides: Chemical Synthesis and uses as Hybridization Probes" Nuceic Acids Research vol. 13 No. 5 1985 pp. 1529-1541.
Barbara C. F. Chu, Geoffrey M. Wahl and Leslie E. Orgel "Derivatization of Unprotected Polynucleotides" Nucleic Acids Research vol. 11 No. 18 1983 pp. 6513-6529.
Tomasz A. Modro and Douglas H. Graham "Phosphoric Amides, 3 Acidic Cleavage of the Phosphorus-Nitrogen Bond in Acyclic and Cyclic Phosphoramidates" J. Org. Chem. 1981 46 pp. 1923-1925.
A Stanley Jones, Christopher McGuigan and Richard T. Walker "Synthesis, Properties, and Biological Activity of some Nucleoside Cyclic Phosphoramidates" J. Chem. Soc. Perkin Trans. 1 1984 pp. 1471-1474.
Hoffmann, Hellmut; Krueger, Bernd-Wieland; Behrenz, Wolfgang 2-(Thi)oxo-1,3,2-oxazaphospholanes and their use as synergists in pesticides 29-Organometallics vol. 96 1982 pp. 633-634.
Paul A. Odorisio, Stephen D. Pastor and John D. Spivack "Reaction of Seven-and Eight-Membered Cyclic Phosphorochloridites with Alkanolamines" Phosphorus and Sulfur 1984 vol. 19 pp. 1-10.
Bernard A. Connolly "Chemical Synthesis of Oligonucleotides containing a free Sulphydryl group and Subsequent attachment of Thiol Specific Probes" Nucleic Acids Research vol. 13 No. 12 1985 pp. 4485-4502.
Tom Maniatis and Argiris Efstratiadis "Fractionation of Low Molecular Weight DNA or RNA in Polyacrylamide Gels Containing 98% Formamide or 7 M Urea" Methods In Enzymology vol. 65 1980 pp. 299-305.
F. Sanger, A. R. Coulson, B. G. Barrell, A. J. H. Smith and B. A. Roe "Cloning in Single-Stranded Bacteriophage as an Aid to Rapid DNA Sequencing" H. Mol. Biol. (1980) 143 pp. 161-178.
Peter H. Schreier and Riccardo Cortese "A Fast and Simple Method for Sequencing DNA Cloned in the Single-Stranded Bacteriophage M13"J. Mol. Biol. (1979) 129 pp. 169-172.
Bowen, E. J., Wokes, Frank, *Fluorescence of Solutions*, pp. 19-45, Longmans, Green & Co., 1953.
Lunney, J., Chrambac, A., Rodbard, D., "Factors Affecting Resolution, Band Width, Number of Theoretical Plates, and Apparant Diffusion Coefficients in Polyacrylamide Gel Electrophoresis", *Analytical Biochemistry* 40, 158-173, 1971.
Pringle, Robert R., Weger, John R., Salser, Winston, DNA Core *Facilities Newsletter*, vol. 1 No. 1, pp. 15-21, May 1, 1988.
Martin, Carole Cooper, "DNA Sequencing in Japan:", *Genetic Engineering News*, pp. 20-21, Sep. 1988.
"Battle of the DNA Sequencers", *Nature*, vol. 333, pp. 477-478, Jun. 2, 1988.
Forster, Leslie S., Livingston, Robert, "The Absolute Quantum Yields of the Fluorescence of Chlorophyll Solutions", *The Journal of Chemical Physics*, vol. 20, No. 8, Aug. 1952.

*Primary Examiner*—Christine M. Nucker
*Assistant Examiner*—Karen I. Krupen
*Attorney, Agent, or Firm*—Steven C. Macevicz; Joseph H. Smith

[57] ABSTRACT

A method is provided for detecting up to four classes of oligonucleotides which have been separated by gel electrophoresis. The method entails labeling members of each class of oligonucleotide with dyes selected from separate sets of dyes so that members of the same class are labeled with dyes from the same set. The four sets of dyes of the invention consist of derivatives of fluorescein, 2',7'-dimethoxy-4', 5'-dichlorofluorescein, tetramethylrhodamine, and rhodamine X carboxylic or sulfonic acid, respectively. Dyes from these sets are spectrally resolvable under conditions of gel electrophoresis.

20 Claims, No Drawings

METHOD OF DETECTING ELECTROPHORETICALLY SEPARATED OLIGONUCLEOTIDES

BACKGROUND

The invention relates generally to molecular separation techniques, and particularly to techniques for identifying oligonucleotides separated by gel electrophoresis.

Many procedures in molecular biology require that heterogeneous mixtures of DNA or RNA be electrophoretically separated into homogeneous components according to mass, charge, conformation, isoelectric point, or the like. The homogeneous components are then detected by densitometry or by radioactive, fluorescent, or chromogenic labeling. Each such method of identification has its own advantages and disadvantages, e.g. Gould and Matthews, *Separation Methods for Nucleic Acids and Oligonucleotides* (North-Holland Publishing Company, Amsterdam, 1976) pgs. 337-344. For example, until recently DNA sequencing techniques relied exclusively on radioactive labels for distinguishing oligonucleotides separated by electrophoresis. Radioactive labels are highly sensitive, and can be readily incorporated into the molecules of interest. However, there are several inherent disadvantages to their use: In autoradiography resolution is limited by the omnidirectional nature of the tracks of the decay particles, the thickness and distance of the autoradiographic emulsion, and the cumulative nature of the signal recorded in the emulsion. Radioactive labels pose a laboratory health hazard, which requires that the labels receive special handling and disposal. And, finally, radioactive labels require long exposure or counting times for adequate signal to noise resolution. This latter disadvantage is especially acute when labels are used in conjunction with automated techniques, such as automated DNA sequencing where bands of different kinds of labeled nucleotides must be rapidly identified as they traverse a single electrophoresis lane. Not only are there no nucleotide-specific radioactive labels for practical identification, but even if there were, current detection techniques such as autoradiography or scintillation counting are too time consuming. As a consequence, fluorescent labeling means have been sought for use with DNA sequencing techniques.

Fluorescent labels can be detected immediately after application; they are conveniently handled; and they permit the precise localization and quantification of the labeled molecules.

Several factors constrain the selection of fluorescent labels for an oligomeric series undergoing separation by gel electrophoresis, such as an oligomeric series of nucleotides whose members differ only in base number. First, the labels must not adversely affect electrophoretic mobility so that extensive band broadening occurs. Nor can the relative effects of the labels on electrophoretic mobility be such that one or more band positions become reversed or overlapping thereby destroying the correspondence between band ordering and the natural order of the oligomeric series. Unfortunately there is no reliable way to predict with certainty the electrophoretic behavior of an oligomer with an arbitrarily chosen label attached, such as an organic dye. Procedures for electrophoretic separations are usually arrived at empirically; however, two major factors determining electrophoretic mobility are charge and molecular weight. Other important factors include configuration of the oligomers and gel polymer density, Gould and Matthews, *Separation Methods for Nucleic Acids and Oligonucleotides* (North-Holland Publishing Company, Amsterdam, 1976), p. 313.

Second, where several distinct labels are required, a selection of dyes cannot have significantly overlapping emission bands. However, given that emission band halfwidth for organic fluorescent dyes is typically about 40-80 nanometers and that the width of the visible spectrum is only about 350-400 nanometers, it is exceedingly difficult to find a suitable selection of fluorescent dyes without significant overlap whenever three or more distinct fluorescent labels are required. Moreover, when several fluorescent dyes are used, excitation becomes difficult because the absorption bands of the dyes are often widely separated. The most efficient excitation occurs when each dye is illuminated at the wavelength corresponding to its absorption band maximum. When several dyes are used together one is often forced to make a trade off between the sensitivity of the detection system and the increased cost of providing separate excitation sources for each dye. Finally, the fluorescent labels must be compatible with the chemistry used to create or manipulate the molecules which are labeled. For example, in enzymatic sequencing of DNA, the fluorescent dyes used to label primers cannot interfere with DNA polymerase activity.

Smith et al, in "Synthesis of Oligonucleotides Containing an Aliphatic Amino Group at the 5' Terminus: Synthesis of Fluorescent DNA Primers for Use in DNA Sequence Analysis," *Nucleic Acids Research*, Vol. 13, pgs. 2399-2412 (1985), disclose a set of four fluorescent dyes for use in enzymatic DNA sequence analysis for labeling oligonucleotides separated by electrophoresis. Each dye from the set is used to identify on an electrophoresis gel bands of oligonucleotides having the same 3' terminal nucleotide.

SUMMARY OF THE INVENTION

In accordance with the method of the invention four sets of fluorescent dyes are used to detect oligonucleotides whenever mixtures of up to four classes of oligonucleotides are separated electrophoretically on a gel. Members from each of the following sets of dyes have been found to be spectrally resolvable with respect to members of every other set under the gel electrophoretic conditions described below.

Set I consists of fluorescein derivatives defined by the formula:

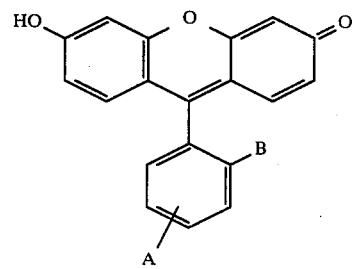

wherein A is a linking functionality at the 5 or 6 carbon position which can be used to link the fluorescein moiety of the dye to a complementary functionality on an oligonucleotide,, and B is an acidic anionic group, preferably carboxyl or sulfonic acid, and most preferably carboxyl.

The following table indicates illustrative linking functionalities represented by A, their complementary functionalities, and the resulting linking groups suitable for use with the invention.

| Linking Functionality | Complementary Functionality | Linking Group |
|---|---|---|
| —NCS | —NH$_2$ | —NHCSNH— |
| ![triazinyl with Cl, Cl] —NH—(triazine with 2 Cl) | —NH$_2$ | —NH—(triazine with Cl, NH—) |
| —SO$_2$X | —NH$_2$ | —SO$_2$NH— |
| —C(O)—O—N(succinimidyl) | —NH$_2$ | —C(O)—NH— |
| —C(O)—O—N(sulfosuccinimidyl, SO$_3^-$) | —NH$_2$ | —C(O)—NH— |
| —NHC(O)—CH$_2$I | —SH | —NHC(O)—CH$_2$S— |
| —N(maleimide) | —SH | —N(succinimide with S—) |

Preferably the linking functionality is isothiocyanate, sulfonyl chloride, 4,6-dichlorotriazinylamine, or succinimidyl carboxylate whenever the complementary functionality is amine. And preferably the linking functionality is maleimide, or iodoacetamide whenever the complementary functionality is sulfhydryl.

Set II consists of derivatives of dichlorodimethoxyfluorescein defined by the formula:

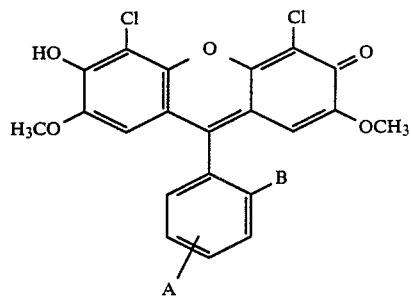

wherein A and B are defined as above.

Set III consists of tetramethylrhodamine derivatized with a linking functionality at the 5 or 6 carbon position, as defined by the formula:

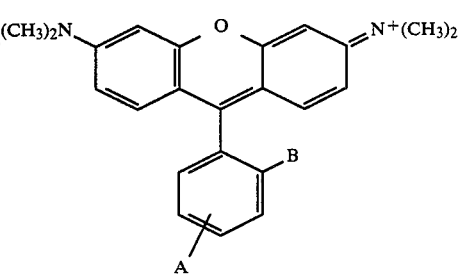

wherein A and B are defined as above.

Set IV consists of rhodamine X derivatives defined by the formula:

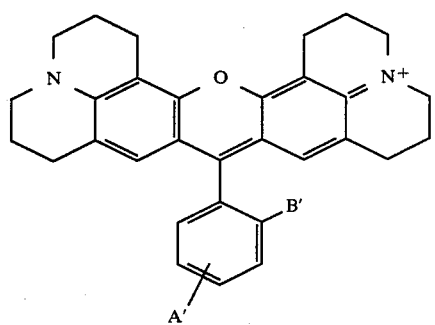

wherein A' is a linking functionality as represented by A (as defined above) or an acidic anionic group as represented by B (as defined above), and B' is an acidic anionic group whenever A' is a linking functionality and B' is a linking functionality whenever A' is an acidic anionic group. More preferably, A' is sulfonic acid or a linking functionality as represented by A, and B' is carboxyl or sulfonic acid whenever A' is a linking functionality, and B' is a linking functionality whenever A' is sulfonic acid. In accordance with the invention, prior to separation, members within each class of oligonucleotides are labeled with a dye selected from the same set to form dye-oligonucleotide conjugates, such that the members of different classes are labeled with dyes from different sets. That is, each class corresponds to a different one of the sets I, II, III, or IV defined above (also referred to herein as the first through fourth sets, respectively). After labeling, the members of all classes are combined to form a mixture. The mixture is then subjected to gel electrophoresis in order to separate the oligonucleotides according to mass, charge, conformation, and/or properties which form the bases of one or two dimensional electrophoretic separations. Oligomeric series with respect to such properties within and among the classes are determined by the relative positions of similarly separated, e.g. bands, of oligonucleotides on the gel. Finally, the dyes attached to the similarly separated oligonucleotides are caused to fluoresce, and the identity of their class is determined by the fluorescence or absorption spectrum of the attached dye.

Class of oligonucleotides can arise in a variety of contexts. For example, they can arise as products of restriction enzyme digests. Preferably, classes identified in accordance with the invention are defined in terms of the terminal nucleotides of nucleic acids so that a correspondence is established between the four possible terminal bases and the four sets of spectrally resolvable dyes. More preferably, the classes arise in the context of chemical or enzymatic sequencing of nucleic acids, and most preferably the classes arise in the context of enzymatic sequencing of DNA. Necessary conditions for a class to be identifiable in accordance with the invention are (1) that the oligonucleotides of the class be capable of separation by gel electrophoresis, (2) that they be capable of labeling by the dyes of the invention, and (3) that the classes be mutually exclusive in that an oligonucleotide can only be a member of one class.

As used herein the term "spectrally resolvable" means that the fluorescent emission bands of the dyes within a set are sufficiently distinct, i.e. sufficiently non-overlapping, from those of the dyes of every other set such that the classes of oligonucleotide to which the dyes are attached can be distinguished by standard photodetection systems.

Oligonucleotide as used herein means a single stranded or double stranded chain of DNA or RNA in the size range of about 10–1000 bases in length (if single stranded), or in the size range of about 10–1000 base pairs in length (if double stranded).

The advantage of these sets of dyes arise from the nature of their spectral properties in gel environments. In particular, the gel environments suitable for electrophoretic separations cause a shift of about 10–15 nm toward the red in the absorption and emission bands of the dyes of sets I and II. Shifting of the absorption bands significantly increases the efficiency with which the dyes can be excited with 514 nm light, a major emission line of the argon ion laser, the most cost effective excitation source. Also, the emission bands of dyes from set I are shifted away from the 514 nm emission line significantly reducing the amount of scattered light collected with the fluorescent signal from these dyes whenever the dyes are illuminated with 514 nm light.

The method of the invention finds direct application to chemical and enzymatic DNA sequencing techniques for fluorescently labeling oligonucleotides separated by gel electrophoresis.

DETAILED DESCRIPTION OF THE INVENTION

The invention includes methods for detecting up to four predefined classes of oligonucleotides that are electrophoretically separated according to mass, charge, conformation, or other property on the same gel. The method is accomplished by labeling oligonucleotides of each class with dyes selected from a separate one of the four sets of dyes defined above. Such labeling ensures that each class has a distinct and spectrally resolvable fluorescent label.

Set I consists of fluorescein mono-derivatized with a linking functionality at either the 5 or 6 carbon position (as determined by the *Color Index* numbering system). Illustrative examples of set I members include fluorescein-5-isothiocyanate, fluorescein-6-isothiocyanate (the -5- and -6-forms being referred to collectively as FITC), fluorescein-5-succinimidylcarboxylate, fluorescein-6-succinimidylcarboxylate, fluorescein-5-iodoacetamide, fluorescein-6-iodoacetamide, fluorescein-5-maleimide, and fluorescein-6-maleimide. These examples of members of set I are available commercially, e.g. Molecular Probes, Inc. (Junction City, OR), or can be synthesized using standard techniques.

Set II consists of 2′,7′-dimethoxy-4′,5′-dichlorofluorescein mono-derivatized with a linking functionality at the 5 or 6 carbon position (the carbons being identified in accordance with the *Color Index* numbering system). Set II members can be obtained by standard modifications of 2,7-dimethoxy-4,5-dichloro-9-(2′,4′-dicarboxyphenyl)-6-hydroxy-3H-xanthen-3-one and 2,7-dimethoxy-4,5-dichloro-9-(2′,5′-dicarboxyphenyl)-6-hydroxy-3H-xanthen-3-one (IUPAC notation) disclosed in U.S. Pat. No. 4,318,846. Accordingly U.S. Pat. No.4,318,846 is incorporated by reference. For example, the 4′ and 5′ carboxys of these compounds can be condensed with N-hydroxysuccinimide using dicyclohexylcarbodiimide to form an amine-selective linking functionality, e.g. as illustrated by examples 6 and 8 of the above-referenced patent (Col. 24–29). Kasai et al., *Anal. Chem.*, Vol. 47, pages 34–37 (1975), discloses the basic technique for such condensations. Accordingly Kasai et al. is incorporated by reference. Set II dyes resulting from such reactions are 2′,7′-dimethoxy-4′,5′-dichlorofluorescein-5-succinimidylcarboxylate and 2,′,7′-dimethoxy-4′,5′-dichlorofluoescein-6-succinimidylcarboxylate (the -5- and -6-forms being referred to collectively as DDFCS).

Set III consists of tetramethylrhodamine mono-derivatized with a linking functionality at either the 5 or 6 carbon position. Illustrative examples of set III members include tetramethylrhodamine-5-isothiocyanate, tetramethylrhodamine-6-isothiocyanate (the -5- and -6-forms being referred to collectively as TMRITC), tetramethylrhodamine-5-iodoacetamide, tetramethylrhodamine-6-iodoacetamide, tetramethylrhodamine-5-succinimidylcarboxylate, tetramethylrhodamine-6-succinimidylcarboxylate, tetramethylrhodamine-5-maleimide, and tetramethylrhodamine-6-maleimide. These exemplary dyes are available commercially, e.g. Molecular Probes, Inc., or can be synthesized using standard techniques.

Set IV consists of rhodamine X derivatives having a disubstituted phenyl attached to the molecule's oxygen heterocycle, one of the substituents being a linking functionality attached to the 4′ or 5′ carbon (IUPAC numbering) of the phenyl, and the other being a acidic anionic group attached to the 2′ carbon. Illustrative examples of set IV members include Texas Red (tradename of Molecular Probes, Inc.), rhodamine X-5-isothiocyanate, rhodamine X-6-isothiocyanate, rhodamine X-5-iodoacetamide, rhodamine X-6-iodoacetamide, rhodamine X-5-succinimidylcarboxylate, rhodamine X-6-succinimidylcarboxylate, rhodamine X-5-maleimide, and rhodamine X-6-maleimide. Most of these exemplary dyes are available commercially, e.g. Molecular Probes, Inc., or can be synthesized using standard techniques.

For example, in the case of Texas Red it can be synthesized according to the procedure disclosed in Titus et al., "Texas Red, a Hydrophilic, Red-Emitting Fluorophore for Use with Fluorescein in Dual Parameter Flow Microfluorometric and Fluorescence Microscopic Studies," *J. Immunological Methods*, Vol. 50, pgs. 193–204 (1982). 5- and 6-carboxy derivatives of rhodamine X can be synthesized using standard techniques, e.g. as disclosed in U.S. Pat. No. 3,932,415, which is incorporated by reference. The 5- or 6-carboxyl groups can then be converted into linking functionalities by standard techniques. For example, rhodamine X-succinimidylcarboxylate is formed by techniques disclosed in Muller et al., *Experimental Cell Research*, Vol. 100, pgs. 213–217 (1976). Accordingly, this reference is incorporated by reference.

The dyes are attached to oligonucleotides using standard procedures, e.g. for a review see Haugland, "Covalent Fluorescent Probes," in *Excited States of Biopolymers*, Steiner, Ed. (Plenum Press, New York, 1983), pgs. 29–58, which pages are incorporated by reference. Recently several techniques have been developed for attaching reactive functionalities to oligonucleotides making it possible to form covalent dye-oligonucleotide conjugates by condensing the reactive functionality on the oligonucleotide with a linking functionality of a dye. For example, Smith et al., cited above, discloses a procedure for attaching an amine group to the 5' end of an oligonucleotide, and Connolly and Rider, "Chemical Synthesis of Oligonucleotides Containing a Free Sulphydryl Group and Subsequent Attachment of Thiol Specific Probes," *Nucleic Acids Research*, Vol. 13, pgs. 4485–4502 (1985), discloses a procedure for attaching sulphydryl groups. Accordingly these two references are incorporated by reference.

Preferably, the reactive, or complementary, functionality on the oligonucleotides is an amine. And preferably the reactive amine is attached by way of the linking agents disclosed in copending U.S. patent application Ser. No. 769,170 filed Aug. 26, 1985, entitled "Amino-derivatized Phosphite and Phosphate Linking Agents, Phosphoramidite Precursors, and Useful Conjugates Thereof." Accordingly this application is incorporated by reference. Most preferably the reactive amine is attached by reacting 2-methoxy-3-trifluoroacetyl-1,3,2-oxazaphosphacyclopentane with the oligonucleotides. Standard electrophoretic procedures are employed for separating the labeled nucleic acids, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 (Springer-Verlag, Berlin, 1984). Preferably the nucleic acids separated are oligonucleotides.

Preferably the type of gel is polyacrylamide having a concentration (weight of volume) of between about 2–20 percent. More preferably, the polyacrylamide gel concentration is between about 4–8 percent. Preferably the gel includes a strand separating, or denaturing, agent. Detailed procedures for constructing such gels are given by Maniatis et al., "Fractionation of Low Molecular Weight DNA and RNA in Polyacrylamide Gels Containing 98% Formamide or 7M Urea," in *Methods in Enzymology*, Vol. 65, pgs. 299–305 (1980); Maniatis et al., "Chain Length Determination of Small Double- and Single-Stranded DNA Molecules by Polyacrylamide Ggel Electrophoresis," *Biochemistry*, Vol. 14, pgs. 3787–3794, (1975); and Maniatis et al., *Molecular Cloning: A Laboratory Manual* (Cold Spring Harbor Laboratory, New York, 1982), pgs. 179–185. Accordingly these references are incorporated by reference. The optimal gel concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20–300 bases have been separated and detected in accordance with the invention in the following gel: 5 percent polyacrylamide made from 25 parts to 1 part acrylamide to bisacrylamide, formed in a Tris-borate EDTA buffer at pH 8.3 (measured at 25° C.) with 48 percent (weight/volume) urea. The gel was run at 50° C.

The dye-oligonucleotide conjugates on the gel are illuminated by standard means, e.g. high intensity mercury vapor lamps, lasers, or the like. Preferably, the dye-oligonucleotides on the gel are illuminated by laser light generated by a argon ion laser, particularly the 488 and 514 nm emission lines of an argon ion laser. Several argon ion lasers are available commercially which lase simultaneously at these lines, e.g. Cyonics, Ltd. (Sunnyvale, CA) Model 2001, or the like.

I. SYNTHESIS OF A PREFERRED LINKING AGENT: 2-METHOXY-3-TRIFLUOROACETYL-1,3,2-OXAZAPHOSPHACYCLOPENTANE

Chloro-N,N-diisopropylaminomethoxy phosphine (5.0 ml, available form Aldrich Chemical Co., Milwaukee, WI) was added dropwise at 0° C. to a stirred solution of N-(2-hydroxyethyl)-2,2,2-trifluoroacetamide (3.9 g) and diisopropylethylamine (5.0 ml) in dichloromethane (about 40 ml) under argon. (N-(2-hydroxyethyl)-2,2,2-trifluoroacetamide is synthesized following the procedures disclosed by Lazarus and Benkovic in *J. Am. Chem. Soc.*, Vol. 101, pgs 4300–4312 (1979): Ethyl trifluoroacetate (56.8 g, 0.4 mol) in 50 mL of chloroform is added dropwise to a stirred solution of 24.4 (0.4 mol) of ethanolamine in 50 mL of chloroform. The solution is stirred at room temperature for 5 h, rotary evaporated to remove the solvent, and distilled at 115° C. (4.3 Torr) to give 58.5 g of oil that crystallized upon scratching.) After stirring at room temperature for 0.5 hours the reaction mixture was washed twice with 0.2M potassium carbonate solution and once with brine, dried (MgSO$_4$), and concentrated under reduced pressure to give N-(2-(N',N'-diisopropylaminomethoxyphosphinyloxy)ethyl)-2,2,2-trifluoroacetamide as a colorless liquid (7.77 g).

$^1$H-NMR (CD$_2$Cl$_2$): δ3.6 (6H, m), 3.4 (3H, d, J=12), 1.2 (12H, d, J=6.5)

$^{31}$P-NMR (CD$_2$Cl$_2$, $^1$H decoupled): δ149(s)

N-(2-(N',N'-diisopropylaminomethoxyphosphinyloxy)ethyl)-2,2,2-trifluoroacetamide (7.7 g) was distilled (58°–59° C. at 0.8 Torr) to quantitatively yield 2-methoxy-3-trifluoroacetyl-1,3,2-oxazaphosphacyclopentane as a colorless liquid.

IR (film): 1705, 1420, 1230, 1200, 1160, 1020, 965 cm$^{-1}$ $^1$H-NMR (CD$_2$Cl$_2$): δ4.45 (2H, m), 3.65 (2H, m), 3.60 (3H, d, J=12)

$^{31}$P-NMR (CD$_2$Cl$_2$, $^1$H decoupled): δ132(s), 125 (q, J=61)

MS: m/e 217 (M+), 197, 148, 136, 123, 120, 109, 92, 79, 70(100), 69, 62

II. REACTING 2-METHOXY-3-TRIFLUOROACETYL-1,3,2-OXAZAPHOSPHACYCLOPENTANE WITH THE 5' TERMINUS OF AN OLIGONUCLEOTIDE TO FORM A 5'-(PROTECTED)-AMINOOLIGONUCLEOTIDE

Attachment of 2-methoxy-3-trifluoroacetyl-1,3,2-oxazaphosphacyclopentane to a 5' hydroxyl of an oligonucleotide was performed on an Applied Biosystems 380A DNA synthesizer (Applied Biosystems, Foster City, CA), or comparable instrument. Caruthers et al, U.S. Pat. No. 4,458,066; Caruthers et al, U.S. Pat. No. 4,415,732; and Caruthers et al, "New Methods for Synthesizing Deoxyoligonucleotides," in *Genetic Engineering*, Vol. 4, pgs. 1-17 (Plenum Press, New York, 1982) provided detailed descriptions of the chemistry used by the Applied Biosystems 380A DNA synthesizer. Accordingly, these references are incorporated by reference for those descriptions. 2-Methoxy-3-trifluoroacetyl-1,3,2-oxazaphosphacyclopentane was used as a 0.2M acetonitrile solution in combination with 0.5M tetrazole/acetonitrile solution to form an activated reagent in the synthesis cycle. The normal synthesizer cycle was modified only during the addition of the activated reagent in the following manner. The activated reagent was added twice with 1 hour wait times after each addition. The coupling yields were about 95%. Normal deprotection with thiophenol/triethylamine and then ammonium hydroxide gave a 5'-aminoethylphosphate oligonucleotide. Similar yields were obtained when the activated reagent comprised an acetonitrile solution containing 0.2M 2-methoxy-3-trifluoroacetyl-1,3,2-oxazaphosphacyclopentane and 0.1M 4-dimethylaminopyridine. In this case the modified activator reagent was added once, and allowed to react for about 2-3 minutes.

III. ATTACHING DYES TO THE AMINO-DERIVATIZED OLIGONUCLEOTIDES

The trifluoroacetyl protection group is removed from the linking agent by treatment with concentrated ammonium hydroxide to give 5'-aminoethylphosphate oligonucleotides. Attachment of the dyes to the exposed amino groups is accomplished by standard procedures, such as the ones described in the following examples.

A. FITC

A DMF solution of FITC (25 microliters at a concentration of 10 mg/ml, e.g. available from Molecular Probes, Inc., Junction City, OR) is added to a solution of 5'-aminoethylphosphate oligonucleotide (an 18-mer) (0.20 micromolar) in water (200 microliters) and 1M NaHCO$_3$/Na$_2$HCO$_3$ buffer, pH 9.0 (25 microliters). The resulting solution is stired in the dark for 6 hours or more. To remove the unconjugated dye, the reaction is passed through an equilibrated 10 ml Sephadex G-25 (medium) (a trademarked product of Pharmacia Fine Chemicals) column with water. The band of colored material eluting in the excluded volume is collected. The crude 5'-fluorescein aminoethylphosphate oligonucleotide is purified by polyacrylamide gel electrophoresis or by HPLC (e.g. Perkin-Elmer Series 4, or comparable device) on a Vydac C18 column (No. 218TP54), or the like, in a linear gradient of 10-20% acetonitrile/0.1M triethylammonium acetate, pH 7.0.

B. TMRITC

A DMF solution of TMRITC (10 microliters at a concentration of 20 mg/ml, e.g. available from Research Organics, Inc., Cleveland, OH, or Molecular Probes, Inc., Junction City, OR) is added to a solution of 5'-aminoethylphosphate oligonucleotide (an 18-mer) (0.004 micromole) in water (88 microliters) and 1M NaHCO$_3$/Na$_2$CO$_3$ buffer, pH 9.0 (2 microliters). The resulting solution is stored in the dark for 6 hours or more. The reaction is passed through an equilibrated 10 ml Sephadex G-25 (medium) column with 0.1M triethylammonium acetate, pH 7.0. The band of colored material in the excluded volume is purified as for FITC.

C. Texas Red

The procedure for attaching Texas Red to the 5'-aminoethylphosphate oligonucleotides can be accomplished by following the same procedure as for TMRITC.

D. DDFCS

DDFCS (0.3 mg) was added to a solution of 5'-aminoethylphosphate oligonucleotide (an 18-mer) (0.006 micromoles in 10 microliters of water) and 1M NaHCO$_3$/Na$_2$CO$_3$ buffer, pH 9.0 (10 microliters). The resulting solution was stored in the dark for 5 hours and worked up as for FITC.

IV. USE OF DYE-AMINOETHYLPHOSPHATE OLIGONUCLEOTIDE CONJUGATES AS PRIMERS IN ENZYMATIC DNA SEQUENCE ANALYSIS

DNA sequence analysis is highly useful, both scientifically and commercially. The two primary techniques for sequencing DNA fragments are chemical methods, e.g., Maxam and Gilbert, *Proc. Nat. Acad. Sci.*, Vol. 74, p. 560 (1970), and enzymatic replication methods, e.g., Smith, *Methods in Enzymology*, Vol. 65, Grossman and Moldave, eds., pgs. 560-580 (Academic Press, New York, 1980), and Sanger et al., *Proc. Natl. Acad. Sci.*, Vol. 74, pgs. 5363-5367 (1977). The method of the invention can be applied with either technique to substitute fluorescent labels for radioactive labels. In this example, it is shown how the subject invention is used in the enzymatic DNA sequencing method of Sanger et al, "Cloning in Single-Stranded Bacteriophage as an Aid to Rapid DNA Sequencing," *J. Mol. Biol.*, Vol. 143, pgs. 161-178 (1980), and Schreier and Cortese, "A Fast Simple Method for Sequencing DNA Cloned in the Single-Stranded Bacteriophage M13," *J. Mol. Biol.*, Vol. 129, pgs. 169-172 (1979), both references being incorporated herein by reference. The DNA sequencing method described by these references will be referred to as the "Sanger method." Before the Sanger method is described, it will be useful to define the following terms.

DNA polymerase is a large multi-function enzyme which catalyzes the synthesis of single-stranded DNA. The particular kind of DNA polymerase used in the Sanger method is the so-called Klenow fragment of *Escherichia coli* DNA polymerase I. This fragment possesses the synthetic function of the enzyme. For synthesis DNA polymerase requires a template, a primer, and a source of deoxyribonucleotides.

A template is a single-stranded piece of DNA which determines the sequence of nucleotides in the single-stranded piece of DNA synthesized by the DNA polymerase. During synthesis, the DNA polymerase moves along the template, and for each nucleotide base thereof, the DNA polymerase attaches the complementary nucleotide to the growing chain of single-stranded DNA. A complementary nucleotide base is one associated with a given base in accordance with the base-pairing rule for the formation of double-stranded DNA. The base-pairing rule requires that adenosine of one strand always be paired with thymidine of the other strand, and that cytidine of one strand always be paired with guanosine of the other strand. Thus, when the DNA polymerase encounters an adenosine on the template, it adds a thymidine to the chain being synthesized, the when it encounters a cytidine, it adds a guanosine. After the DNA polymerase moves on, the newly synthesized chain and the complementary portion of the template are in double-stranded form.

A primer is a fragment of single-stranded DNA. The primer provides a starting location for the DNA polymerase to begin adding nucleotides in the synthesis process. The primer must be annealed to the piece of single-stranded DNA containing the template so that a section of double-stranded DNA is provided as the starting point for the DNA polymerase.

Dideoxyribonucleotides are identical to deoxyribonucleotides except that they lack both the 2' and 3' hydroxyl groups on the ribose moiety, instead of just the 2' hydroxyl as with deoxyribonucleotides. Dideoxyribonucleotides are sometimes referred to as analogs of deoxyribonucleotides, in that DNA polymerase accepts the dideoxy derivatives in place of the corresponding deoxyribonucleotide in the DNA synthesis process. When such a substitution takes place, synthesis stops because the DNA polymerase has no 3' hydroxy group on which to attach the subsequent nucleotide.

In the Sanger method a DNA strand to be sequenced is used as a template for *Escherichia coli* DNA polymerase I. A primer is annealed to a piece of single-stranded DNA containing the template, and then it is extended enzymatically to an average of 20 to 300 or more nucleotides in the presence of radioactively labeled deoxyribonucleoside triphosphates, e.g. $^{32}$P-labeled adenosine triphosphate, and the dideoxyribonucleoside triphosphate analog of one of the four nucleotides. That is, four separate reactions are carried out each including a different dideoxy analog. Because DNA chain growth requires the addition of deoxyribonucleotides to the 3'-hydroxyl, incorporation or a dideoxyribonucleotide terminates chain growth. Incorporation of the dideoxy analog in place of the normal nucleotide occurs randomly, so that each of the four reactions generates a heterogeneous population of labeled strands terminating with the same nucleotide, which can be separated electrophoretically according to chain length. That is, four classes of oligonucleotides are established based on the type of terminal dideoxyribonucleoside which is present. A single stranded DNA phage M13 is used to clone copies of the DNA fragment to be sequenced. When a sufficient quantity of M13 is cloned, the M13 DNA is purified and separated into four aliquots. In each aliquot the synthesis or chain growth reaction takes place in the presence of the respective dideoxyribonucleotides.

In accordance with the invention, instead of labeling oligonucleotides by incorporation of radioactive nucleotides during the chain growth phase, primers are synthesized and then labeled by attaching a linking functionality and reacting it with a dye. Preferably an amine linking functionality is attached by reacting the primers with 2-methoxy-3-trifluoroacetyl-1,3,2-oxazaphosphacyclopentane to form 5'-(protected)aminoethylphosphate oligonucleotides. The protecting groups are removed and a dye of the invention is attached to the deprotected 5'-amine to form dye-primer conjugates. The dye-primer conjugates are then used in accordance with Sanger's method, with the exception that oligonucleotides from the four aliquots are mixed together and loaded onto the same electrophoresis lane. The relative size of the oligonucleotides and the nature of their terminal dideoxyribonucleotides are determined as bands of homogeneous oligonucleotides travel down the electrophoresis lane and are detected by a fluorimeter or spectrophotometer after illumination. In accordance with the invention the bands are preferably illuminated with both 514 nm and 488 nm laser limit, either sequentially or simultaneously.

We claim:

1. A method for detecting up to four classes of oligonucleotides separated by gel electrophoresis, the method comprising the steps of:
labeling each oligonucleotide within each class with one or more dyes selected from the same one of either a first set of dyes, a second set of dyes, a third set of dyes, or a fourth set of dyes to form dye-oligonucleotide conjugates from each class such that oligonucleotides from the same class are labeled with dyes from the same set and oligonucleotides from different classes are labeled with dyes from different sets, the first set consisting of dyes defined by the formula:

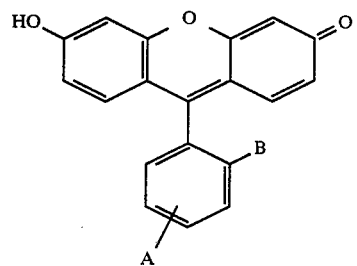

wherein A is a linking functionality and B is an acidic anionic group, the second set consisting of dyes defined by the formula:

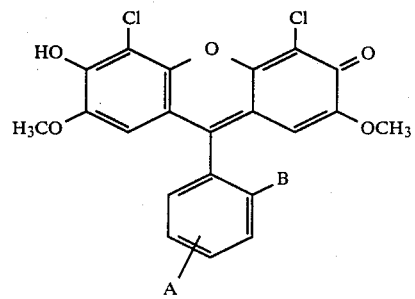

wherein A and B are defined as above, the third set consisting of dyes defined by the formula:

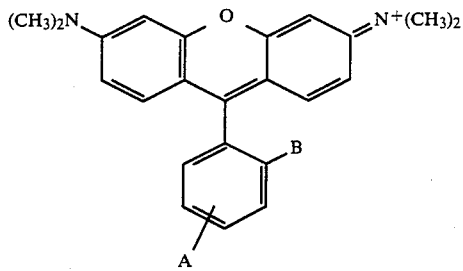

wherein A and B are defined as above, and the fourth set consisting of dyes defininied by the formula:

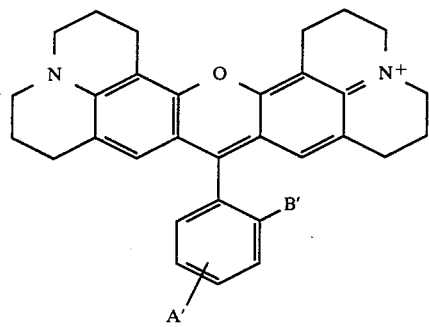

wherein A' is a linking functionality or an acidic anionic group and B' is a linking functionality whenever A' is an acidic anionic group, and B' is an acidic anionic group whenever A' is a linking functionality;

forming a mixture of the dye-oligonucleotide conjugates from more than one class;

electrophoretically separating the dye-oligonucleotide conjugates on a gel;

illuminating the dyes of similarly separated dye-oligonucleotide conjugates; and identifying the class of similarly separated dye-oligonucleotide conjugates by the fluorescence or absorption spectrum of the dyes of the dye-oligonucleotide conjugates.

2. The method of claim 1 wherein said acidic anionic group of said substituent A', B, or B' is carboxylic acid or sulfonic acid.

3. The method of claim 2 wherein said step of identifying includes identifying similarly separated dye-oligonucleotide conjugates by the fluorescence spectrum of the dyes of the dye-oligonucleotide conjugates.

4. The method of claim 3 wherein said step of labeling includes attaching a complementary functionality to each oligonucleotide of each of said four classes of oligonucleotide.

5. The method of claim 4 wherein said gel is a polyacrylamide gel having a concentration of between about 2-25 percent.

6. The method of claim 5 wherein said linking functionalities represented by A are amine selective and said complementary functionalities are amines.

7. The method of claim 6 wherein said first set consists of fluorescein-5-isothiocyanate, fluorescein-6-isothiocyanate, fluorescein-5-succinimidylcarboxylate, and fluorescein-6-succinimidylcarboxylate; said second set consists of 2',7'-dimethoxy-4',5'-dichlorofluorescein-5-succinimidylcarboxylate, and 2',7'-dimethoxy-4',5'-dichlorofluorescein-6-succinimidylcarboxylate; said third set consists of tetramethylrhodamine-5-isothiocyanate, tetramethylrhodamine-6-isothiocyanate, tetramethylrhodamine-5-succinimidylcarboxylate, and tetramethylrhodamine-6-succinimidylcarboxylate; and said fourth set consists of Texas Red, rhodamine X-5-isothiocyanate, rhodamine X-6-isothiocyanate, rhodamine X-5-succinimidylcarboxylate, and rhodamine X-6-succinimidylcarboxylate.

8. The method of claim 7 wherein said step of attaching said complementary functionality includes reacting a 2-substituted-3-protected-1,3,2-oxazaphosphacycloalkane with said oligonucleotides.

9. The method of claim 8 wherein said 2-substituted-3-protected-1,3,2-oxazaphosphacycloalkane is 2-methoxy-3-trifluoroacetyl-1,3,2-oxazaphosphacyclopentane.

10. The method of claim 7 wherein said step of illuminating includes illuminating said dyes with 514 nm light.

11. The method of claim 10 wherein said step of illuminating includes illuminating said dyes with 488 nm light.

12. A method of distinguishing oligonucleotides having different terminal dideoxyribonucleotides in the enzymatic method of DNA sequencing, the method comprising the steps of:

linking a first dye to the 5' termini of oligonucleotides of a predetermined sequence to form a first plurality of labeled primers, the first dye being selected from the group defined by the formula:

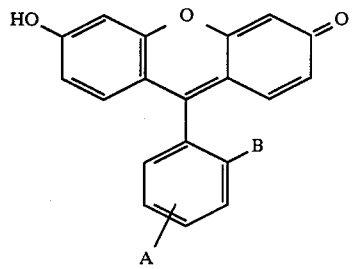

wherein A is a linking functionality and B is an acidic anionic group;

linking a second dye to the 5' termini of oligonucleotides of the predetermined sequence to form a second plurality of labeled primers, the second dye being selected from the group defined by the formula:

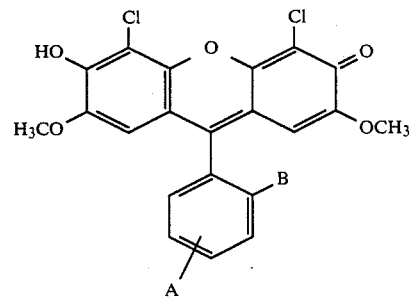

wherein A and B are defined as above;

linking a third dye to the 5' termini of oligonucleotides of the predetermined sequence to form a third plurality of labeled primers, the third dye being selected from the group defined by the formula:

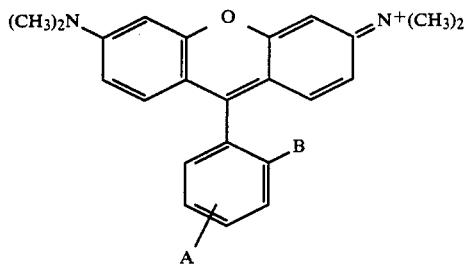

wherein A and B are defined as above;
linking a fourth dye to the 5' termini of oligonucleotides of the predetermined sequence to form a fourth plurality of labeled primers, the fourth dye being selected from the group defined by the formula:

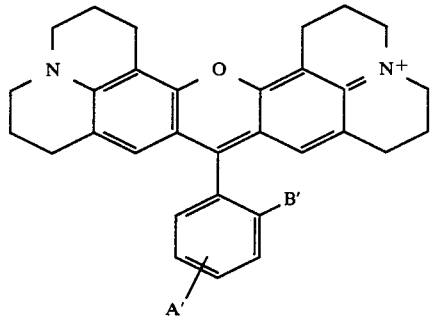

wherein A' is a linking functionality or an acidic anionic group, and B' is a linking functionality whenever A' is an acidic anionic group and B' is an acidic anionic group whenever A' is a linking functionality;
using the first, second, third, and fourth pluralities of labeled primers to separately generate labeled oligonucleotides in accordance with the enzymatic DNA sequencing procedure such that a one-to-one correspondence is established between the pluralities of labeled primers and the kind of dideoxyribonucleotide attached to the 3' terminus of the labeled oligonucleotide;
mixing the labeled oligonucleotides;
electrophoretically separating the labeled oligonucleotides on a gel according to size;
illuminating similarly separated labeled oligonucleotides; and
identifying the kind of dideoxyribonucleotide attached to the 3' terminus of similarly separated labeled oligonucleotides by relating the respective fluorescence or absorption spectrum of the similarly separated labeled oligonucleotides to the attached dideoxyribonucleotide.

13. The method of claim 12 wherein said acidic anionic group of said substituent A', B, or B' is carboxylic acid or sulfonic acid.

14. The method of claim 13 wherein said step of identifying includes identifying said similarly separated labeled oligonucleotides by said fluorescence spectrum of said dyes attached to said labeled primers of the labeled oligonucleotides.

15. The method of claim 14 wherein said steps of linking includes attaching a complementary functionality of said 5' termini of said oligonucleotides of said predetermined sequence.

16. The method of claim 15 wherein said gel is a polyacrylamide gel having a concentration of between about 2–25 percent.

17. The method of claim 16 wherein said linking functionalities represented by A are amine selective and said complementary functionalities are amines.

18. The method of claim 17 wherein said first dye is selected from the group consisting of fluorescein-5-isothiocyanate, fluorescein-6-isothiocyanate, fluorescein-5-succinimidylcarboxylate, and fluorescein-6-succinimidylcarboxylate; said second dye is selected from the group consisting of 2',7'-dimethoxy-4',5'-dichlorofluorescein-5-succinimidylcarboxylate, and 2',7'-dimethoxy-4',5'-dichlorofluorescein-6-succinimidylcarboxylate; said third dye is selected from the group consisting of tetramethylrhodamine-5-isothiocyanate, tetramethylrhodamine-6-isothiocyanate, tetramethylrhodamine-5-succinimidylcarboxylate, and tetramethylrhodamine-6-succinimidylcarboxylate; and said fourth dye is selected from the group consisting of Texas Red, rhodamine X-5-isothiocyanate, rhodamine X-6-isothiocyanate, rhodamine X-5-succinimidylcarboxylate, and rhodamine X-6-succinimidylcarboxylate.

19. The method of claim 18 wherein said step of attaching said complementary functionality includes reacting a 2-substituted-3-protected-1,3,2-oxazaphosphacycloalkane with said oligonucleotides of said predetermined sequence.

20. The method of claim 19 wherein said 2-substituted-3-protected-1,3,2-oxazaphosphacycloalkane is 2-methoxy-3-trifluoroacetyl-1,3,2-oxazaphosphacyclopentane.

* * * * *